United States Patent
Trainoff

(10) Patent No.: US 9,638,546 B2
(45) Date of Patent: May 2, 2017

(54) CORROSION RESISTANT PRESSURE TRANSDUCER

(71) Applicant: Wyatt Technology Corporation, Santa Barbara, CA (US)

(72) Inventor: Steven P. Trainoff, Goleta, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 109 days.

(21) Appl. No.: 14/646,717

(22) PCT Filed: Nov. 27, 2013

(86) PCT No.: PCT/US2013/072428
§ 371 (c)(1),
(2) Date: May 21, 2015

(87) PCT Pub. No.: WO2014/085721
PCT Pub. Date: Jun. 5, 2014

(65) Prior Publication Data
US 2015/0292904 A1   Oct. 15, 2015

Related U.S. Application Data

(60) Provisional application No. 61/732,035, filed on Nov. 30, 2012.

(51) Int. Cl.
G01L 9/14 (2006.01)
G01L 9/10 (2006.01)
(Continued)

(52) U.S. Cl.
CPC ............... G01D 5/12 (2013.01); G01L 9/007 (2013.01); G01L 13/025 (2013.01); G01L 19/0654 (2013.01); G01N 11/08 (2013.01)

(58) Field of Classification Search
CPC ..... G01L 9/10; G01L 9/14; G01L 9/00; G01L 9/007; G01L 13/02; G01L 13/06;
(Continued)

(56) References Cited

U.S. PATENT DOCUMENTS 3,946,615 A * 3/1976 Hluchan .................. G01L 9/10
336/30
4,517,842 A * 5/1985 Twomey ............... G01L 11/006
73/701
(Continued)

FOREIGN PATENT DOCUMENTS

CH        0947815 A1 * 10/1999 ............. G01L 9/007
DE        2835523 A1 *  2/1980 ............. G01L 9/007
(Continued)

Primary Examiner — Nguyen Ha
(74) Attorney, Agent, or Firm — David N. Villalpando

(57) ABSTRACT

A pressure transducer is disclosed wherein no wetted areas have been welded. A cavity is milled into the back of each of the blocks of a material which will make up the body of the transducer. Pickup coils are placed into these cavities and are held in place generally with epoxy cement. With the coils mounted within the sensor body, the surface which will be exposed to the sample or reference fluids is comprised of a single, solid material with no welding joints. Further, as the sensor block half is made of a single, solid material, fluid fitting connections may be machined directly into the body. The pickup coil placed within the improved sensor body may be wound on an open frame of nickel superalloy (NiSA). Another embodiment involves coating or encapsulating the sensing membrane within a soft, non-magnetic material protecting it from corrosion.

11 Claims, 4 Drawing Sheets

(51) Int. Cl.
  *G01L 13/02* (2006.01)
  *G01L 13/06* (2006.01)
  *G01L 19/06* (2006.01)
  *G01N 11/08* (2006.01)
  *G01D 5/12* (2006.01)
  *G01L 9/00* (2006.01)

(58) Field of Classification Search
  CPC ....... G01L 13/00; G01L 13/025; G01L 19/06; G01L 19/0654; G01N 11/08
  See application file for complete search history.

(56) References Cited

U.S. PATENT DOCUMENTS

| | | | | |
|---|---|---|---|---|
| 4,538,465 | A * | 9/1985 | Bianchi | G01L 9/007 336/30 |
| 4,665,753 | A * | 5/1987 | Bertrand | G01L 13/025 336/30 |
| 5,705,751 | A * | 1/1998 | Briefer | G01D 5/202 73/722 |
| 6,484,586 | B1 * | 11/2002 | Dutoit | G01L 9/007 73/722 |
| 7,469,878 | B1 * | 12/2008 | Richard | F16K 31/0651 251/129.06 |
| 2007/0095146 | A1 * | 5/2007 | Brosh | G01L 9/0085 73/722 |
| 2009/0007683 | A1 * | 1/2009 | Kaneko | G01L 9/007 73/728 |
| 2009/0326839 | A1 * | 12/2009 | Rogers | G01F 1/3209 702/47 |

FOREIGN PATENT DOCUMENTS

| | | | | |
|---|---|---|---|---|
| GB | 1525982 | A * | 9/1978 | ............ G01L 9/007 |
| JP | 2010151737 | A * | 7/2010 | ............ G01L 9/10 |
| JP | 2012093107 | A * | 5/2012 | ............ G01L 19/06 |

* cited by examiner

CORROSION RESISTANT PRESSURE TRANSDUCER

BACKGROUND

Viscometry is a widely used measurement method to help determine the physical properties of particles and molecules in solution. Generally used in conjunction with size exclusion chromatography (SEC), also known as high performance liquid chromatography (HPLC), these instruments measure the differential viscosity between a sample bearing solution and a reference liquid, and are hence referred to as differential viscometers. The specific viscosity of the sample may then be determined, and from this value, and knowledge of the sample concentration, the intrinsic viscosity of the sample may be derived. When viscometric and concentration measurements are further coupled with multi-angle light scattering measurements, further information regarding molecular conformation and molecular interactions may be determined.

A critical, and expensive, component of differential viscometers is the pressure transducer. As sample fluids flow through the transducer, its wetted surfaces are prone to corrosion due to exposure to the sample solvent. It is an objective of the present invention to provide a transducer with sensor bodies which are highly corrosion resistant. Another wetted element of viscometer is the sensing membrane which is generally sandwiched between two pressure transducer halves. This element is also susceptible to corrosion. It is a further objective of this invention to improve the lifetime of the sensing membrane.

BRIEF DESCRIPTION OF THE INVENTION

A new pressure transducer sensor body is disclosed which may be fabricated by milling a cavity into the back of a block of a material such as 316 stainless steel. The pickup coils of the transducer are placed into these cavities may be held in place with epoxy cement. With the coils mounted within the sensor body, the surface of the sensor body which will be exposed to the sample or reference fluids is comprised of a single, solid material with no welding joints. Further, as the sensor block half is made of a single, solid material, fluid fitting connections may be machined directly into the body, obviating the need add and weld fitting connectors into the sensor block, thus providing a new design which is simpler, less prone to leakage, and less expensive than conventional designs. In another embodiment of the invention, the pickup coil placed within the improved sensor body may be wound on an open frame of nickel superalloy (NiSA), improving the concentration of magnetic field lines across the sensing membrane, thereby increasing the sensitivity of the measurement. Another embodiment of the present invention involves coating or encapsulating the sensing membrane within a soft, non-magnetic material such as Teflon to protect it from corrosion. Further, because it is encapsulated, a wider variety of materials may be used for the membrane itself.

DETAILED DESCRIPTION OF THE INVENTION

Figure 1:
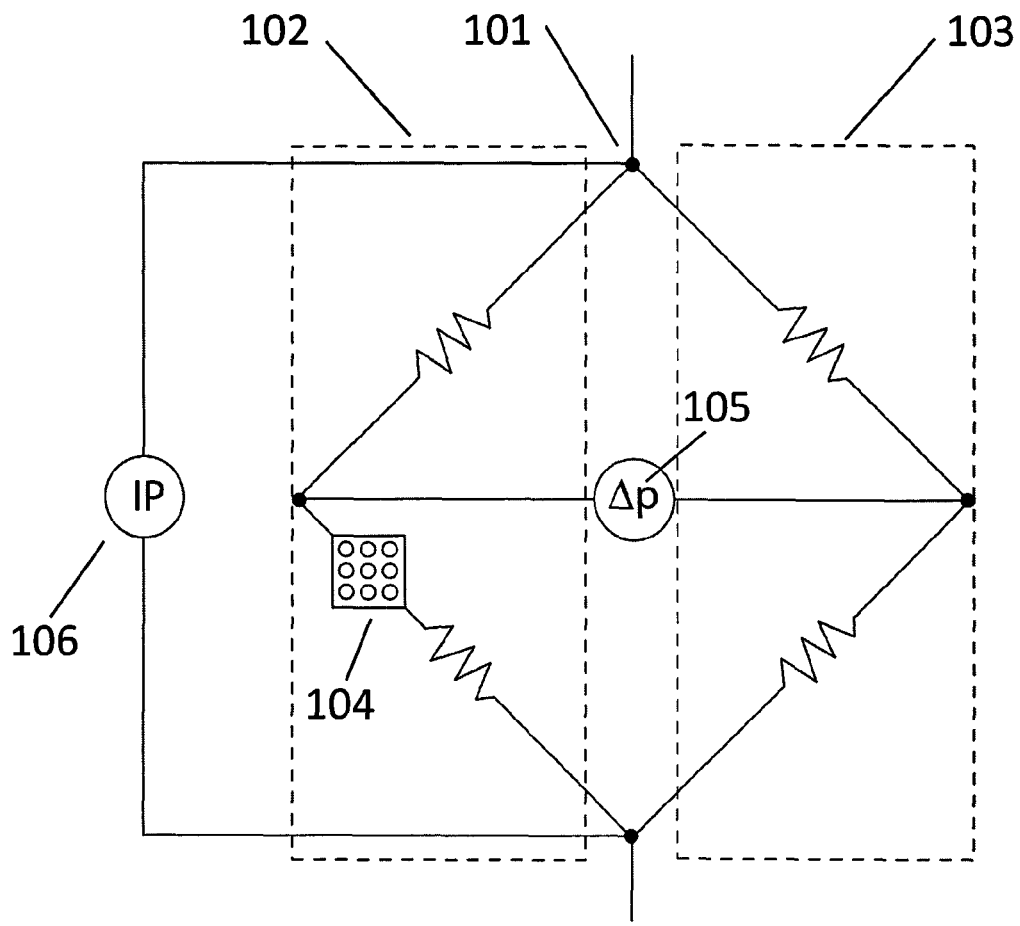
FIG. 1 is a depiction of a capillary bridge viscometer including a pressure transducer.

Most viscometers for use with high performance liquid chromatography (HPLC) systems utilize a capillary bridge design, as shown in FIG. 1. The fluid stream splits at the top of the bridge 101, and half of the sample flows through each bridge arm 102 and 103. Since the bridge is symmetric, the differential pressure transducer in the center of the bridge measures zero when all four arms are filled with solvent. When a sample is injected it flows into both arms. One arm of the bridge 102 contains an additional delay volume 104 so that the sample enters the delay volume 104, but the pure solvent that was present prior to sample injection exits, causing a pressure imbalance in the bridge which is measured by a pressure transducer 105 in the center of the bridge. This imbalance pressure, combined with the inlet pressure measured by a separate pressure transducer 106 between the top and bottom of the bridge, gives the specific viscosity through the relation $$\eta_{sp} = \frac{\eta}{\eta_0} - 1 = \frac{4\Delta p}{IP - 2\Delta p}$$

where $\eta$ is the viscosity of the sample, and $\eta_0$ is the viscosity of the solvent, $\Delta p$ is the imbalance pressure across the bridge, and IP is the pressure from top to bottom of the bridge. This is a direct measurement of the specific viscosity that depends only on the calibrated transducers. At the end of the run, the delay volume is flushed with new solvent and a new measurement can be performed.

When combined with a concentration detector, the viscometer may be used to compute the intrinsic viscosity $[\eta]$, which is defined as $$[\eta] = \lim_{c \to 0} \eta_{sp}/c.$$

The intrinsic viscosity measurements may be complimented by measuring the molar mass of the particles or molecules in solution through use of a light scattering detector to make multi-angle light scattering (MALS) measurements. The data can be used to generate Mark-Houwink plots, which are plots of $\text{Log}([\eta])$ vs. $\text{Log}(M)$, where M is the molar mass of the sample. A fit to this data to the Mark-Houwink equation $$[\eta] = KM^\alpha$$

yields the coefficients K and $\alpha$ which are measures of molecular conformation and the molecules' interaction with the solvent.

Viscometers may also be used to determine the hydrodynamic volume, which is the volume of a sphere that has the same intrinsic viscosity of the sample being measured, through the Einstein-Simha relation $$V_h = M[\eta]/(2.5 N_a)$$

where $V_h$ is the hydrodynamic volume, M is the molar mass measured with a MALS detector, and $N_A$ is Avogadro's number. The hydrodynamic radius can then be derived from the hydrodynamic volume by the relation $$r_h=(3V_h/4\pi)^{1/3}.$$

All of the above information regarding sample characteristics can only be obtained reliably with a proper measurement of the differential pressure across the pressure transducers. These elements, therefore, are of critical importance to any bridge viscometer, and any degradation of any of the elements thereof can result in erroneous values.

Figure 2:
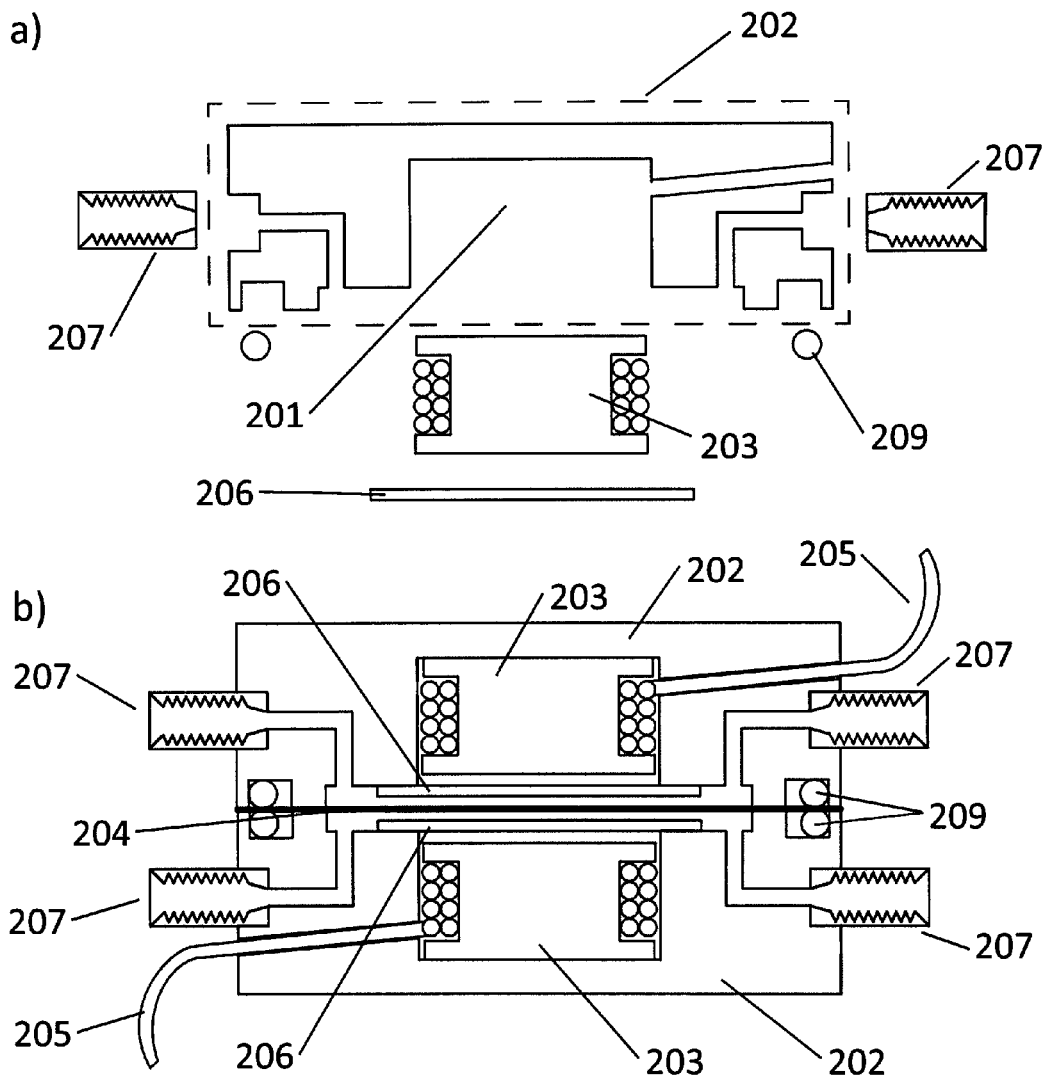
FIG. 2 shows a design of a conventional pressure transducer.

There are many different designs for pressure transducers that are intended for wet and dry operation. Most designs have to make a tradeoff between best sensitivity, linearity, and hysteresis, and corrosion resistance. A common design, typically known as variable reluctance, for a conventional transducer, such as that manufactured by Validyne Engineering Corporation (Northridge, Calif.), is depicted in FIG. 2. FIG. 2a shows a deconstructed view of a single half of the pressure transducer. The complete transducer consists of two sensor bodies 202 that contain magnetic pickup coils 203. Suspended between the two is a magnetic membrane 204 that is in contact with the pressure media. When there is a pressure difference between the two sides of the transducer, the membrane 204 flexes in response. The mean position of the membrane is detected by running the magnetic pickup coils 203 in an AC bridge configuration. The sensor bodies 202 are generally fabricated by milling a cavity 201 in a block of 410 stainless steel. The pickup coils 203 are fixed into the cavity 201 by epoxy cement, and the wires 205 are threaded through access holes in the side. The cavity is typically sealed with a cap of 0.010" foil 206 comprised of an austenitic nickel-chromium-based superalloy, such as Inconel® produced by Special Metals Corporation (New Hartford, N.Y.). The foil is microwelded to form a liquid tight seal. The two transducer body halves are connected together, sandwiching therebetween the magnetic membrane 204, and the assembly is sealed with O-rings 209 and connected with bolts or other suitable connecting means. Fluid connections 207 generally made from less corrosive 316 stainless steel are welded or otherwise connected to the transducer bodies 202 The objectives of this traditional design are two-fold. By making the body of 410 stainless steel, which is a magnetic alloy, the body forms a magnetic pole piece the concentrates the magnetic field of the solenoid. The Inconel cap is magnetically invisible so it does not form part of the magnetic return circuit. One advantage of this design is that changing the thickness of the membrane, allows the user to change the pressure range.

While this design works well for non-corrosive solvents, if performs poorly with many aqueous salt solutions. The magnetic alloy 410 stainless is not particularly corrosion resistant. However, the largest limitation of the design is the microweld between the stainless steel body 202 and the Inconel cap 206 that seals in the magnetic pickup coil 203. The weld, by virtue being an intermediate alloy between Inconel and 410 stainless steel is susceptible to corrosion. When corrosion occurs at the weld, the pickup coils 203 are exposed to the solvent and the entire costly device is generally destroyed.

While the transducer membrane, which is also traditionally made of 410 stainless, is also susceptible to corrosion, if it is compromised it can simply be replaced. After the membrane is replaced, the new assembly is reassembled and recalibrated, which is a relatively inexpensive repair.

Figure 3:
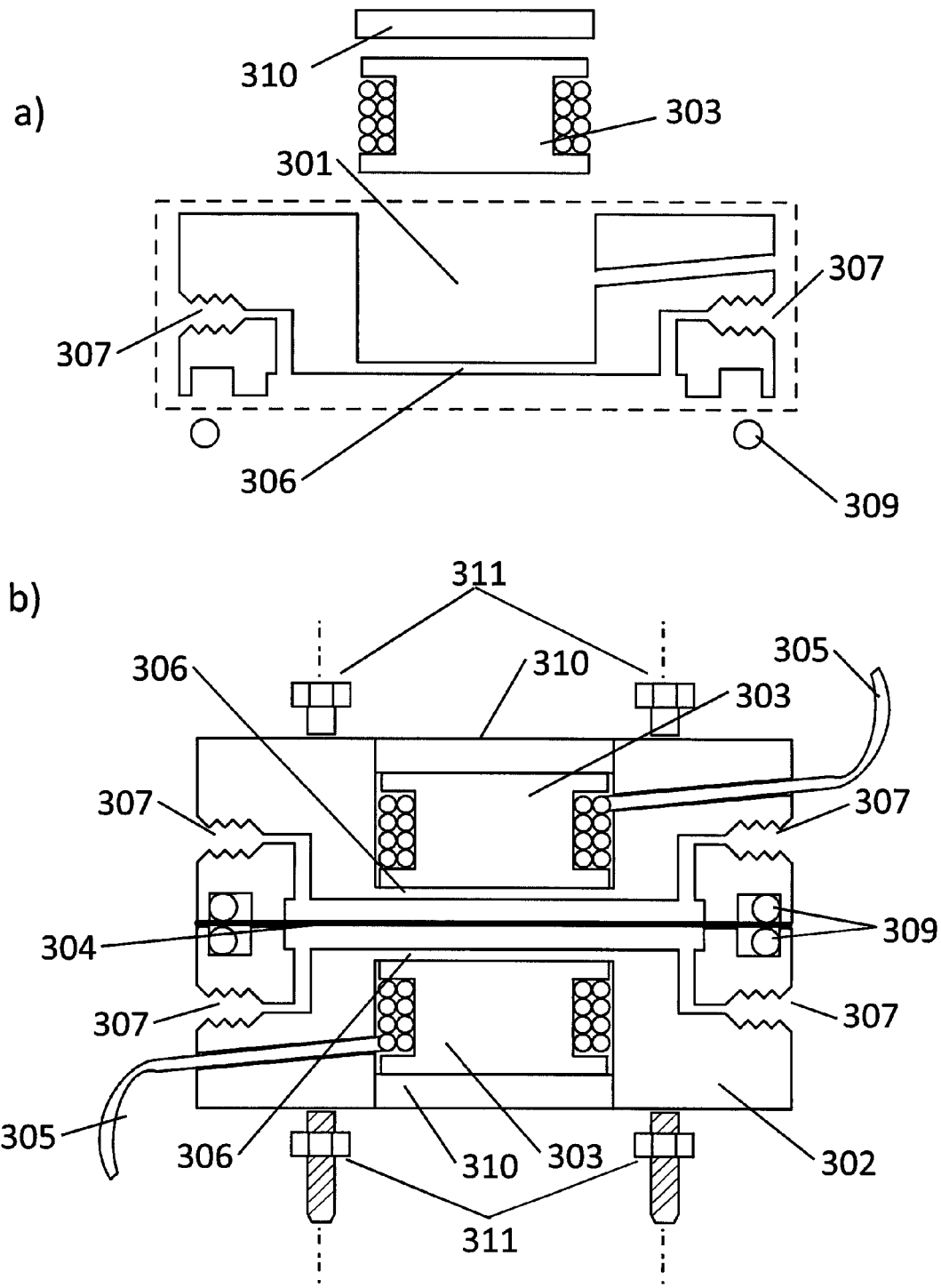
FIG. 3 an embodiment of the present inventive transducer.

FIG. 3 shows a cross section of an embodiment of the present inventive, corrosion resistant pressure transducer which eliminates the microwelded Inconel cap, making it thus impossible for the sample or reference fluids to come in contact with the pickup coils. FIG. 3a shows a deconstructed view of a single half of the pressure transducer. In this embodiment the pocket 301 that holds the electrical pickup coils 303 is milled from the back of the transducer body 302. The pickup coil 303 is mounted with epoxy cement or other suitable material forming a plug 310, and the electrical connections 305 come out the side as in the conventional design. Once the coils 303 are mounted, the entire assembly may be machined flat so that the metal 306 above the pickup coil 303 is roughly the same thickness as in the conventional design of FIG. 2, generally about 0.010" nominal between the surface and the magnetic membrane 304. Since the body is not manufactured from 410 stainless, the fluid fittings 307 can be machined directly into the block. By eliminating the welding steps, the new transducer is not only more corrosion resistant, it is less complicated, and therefore less expensive to manufacture. As in the transducer shown in FIG. 2, the transducer sensing membrane 304 is sandwiched between two transducer bodies, generally sealed with O-rings 309, and the two transducer bodies are connected together by bolts 311 or another clamping means.

Figure 4:
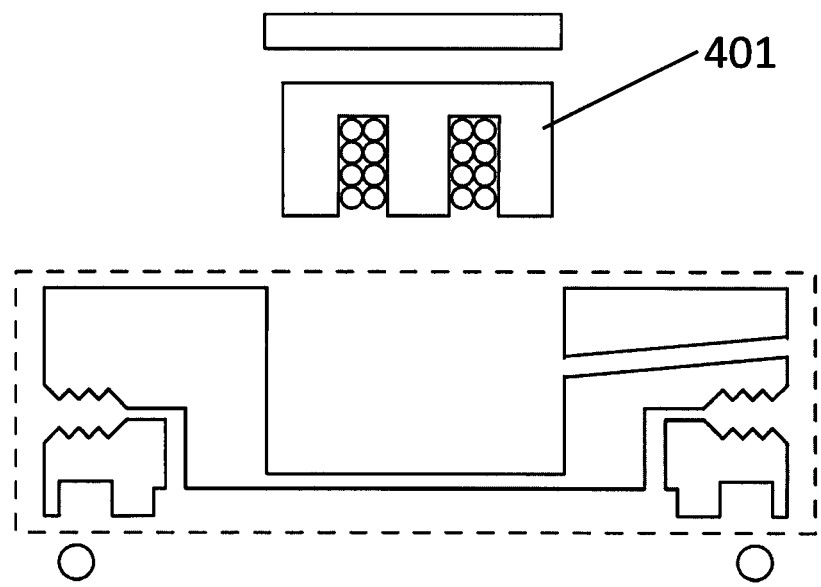
FIG. 4 depicts another embodiment of the invention wherein the coils are wound around an open frame.

The body of the inventive transducer is generally constructed from 316 stainless steel, which has much better corrosion resistance than 410 stainless. However because 316 stainless is not magnetic, it does not help to concentrate the magnetic field. Therefore in the simplest embodiment, the signal from the AC bridge drops by roughly a factor of two. However in all other respects the electrical behavior is identical to the standard variable reluctance design. In a further embodiment of the invention the sensitivity lost by changing the body from 410 to 316 stainless is recovered. Since the inventive transducer separates the fluid handling from the magnetic properties, the pickup coil can be wound on an open frame of nickel superalloy (NiSA) as shown in FIG. 4. The NiSA open frame spool 401 performs the same role as the body in the conventional pressure transducer shown in FIG. 2. The use of NiSA open frame spools concentrates the magnetic field and compensates for the sensitivity lost by the material of the body.

In another embodiment of the invention, the sensing membrane is encapsulated in a soft, non-magnetic material such as Polytetrafluoroethylene, or Teflon (E. I. du Pont de Nemours and Company). The coating does not appreciably change the performance of the sensor, but it prevents corrosive solvents from coming into direct contact with membrane. Typically Teflon coatings have micro-pores so the underlying material may eventually corrode, but the lifetime is dramatically increased. 410 stainless steel is a reasonable sensor material because it is has a relatively high magnetic susceptibility, has low coercivity, and is very elastic. This minimizes sensor hysteresis. However because the sensor membrane will be encapsulated in this embodiment, one may use a wider range of materials such as NiSA that has a much higher magnetic susceptibility and therefore improves the device sensitivity.

While many references have been made to viscometers throughout this specification, the inventive transducer disclosed herein should not be considered limited to use with viscometers or viscometric measurements. Indeed, the embodiments disclosed herein have many advantages over conventional pressure transducers which are susceptible to corrosion.

There are many embodiments of our invention that will be obvious to those skilled in the arts of pressure measurements and viscometry that are but simple variations of the basic invention herein disclosed that do not depart from the fundamental elements that have been listed for their practice; all such variations are but obvious implementations of the invention described hereinbefore and are included by reference to our claims, which follow.

The invention claimed is:

1. An improved pressure transducer wherein fluids being measured do not come into contact with any welded surfaces comprising
   a. two transducer body halves, each of which comprises
      i. an empty cavity containing a pickup coil sealed into place;
      ii. fluid entrance and exit ports;
      iii. an unbroken surface over which a fluid sample may pass from said entrance port to said exit port without encountering any welds;
   b. a magnetic sensing membrane placed between the two transducer body halves capable of flexing in response to a pressure difference there across;
   c. fluid sealing means between the two transducer body halves and the magnetic sensing membrane; and
   d. connection means to connect the two halves of the transducer together.

2. The pressure transducer of claim 1 wherein said pickup coils are sealed into place with epoxy cement.

3. The pressure transducer of claim 2 wherein said epoxy cement further comprises a plug which extends from the pickup coil to the top surface of each of the pressure transducer body halves.

4. The pressure transducer of claim 1 wherein said transducer body halves are manufactured of 316 stainless steel.

5. The pressure transducer of claim 1 wherein said empty cavity into which said pickup coil is sealed into place in each of said transducer body halves is milled from the side of the pressure transducer half opposite said unbroken surface over which said fluid sample passes from said entrance port to said exit port.

6. The pressure transducer of claim 1 wherein said magnetic sensing membrane is coated or encapsulated in a non-corrosive material.

7. The pressure transducer of claim 6 wherein said magnetic sensing membrane is coated or encapsulated in Teflon.

8. The pressure transducer of claim 6 wherein said magnetic sensing membrane is comprised of 410 stainless steel.

9. The pressure transducer of claim 6 wherein said magnetic sensing membrane is comprised of nickel superalloy (NiSA).

10. The pressure transducer of claim 1 wherein said pickup coil is wound on an open frame spool.

11. The pressure transducer of claim 10 wherein said open frame spool is comprised of nickel superalloy (NiSA).

* * * * *